(12) United States Patent
Paltieli (10) Patent No.: US 6,216,029 B1
(45) Date of Patent: Apr. 10, 2001

(54) FREE-HAND AIMING OF A NEEDLE GUIDE

(75) Inventor: Yoav Paltieli, Haifa (IL)

(73) Assignee: Ultraguide Ltd., Tirat Kakarmel Industrial Park (IL)

( * ) Notice: Subject to any disclaimer, the term of this patent is extended or adjusted under 35 U.S.C. 154(b) by 0 days.

(21) Appl. No.: 08/983,100

(22) PCT Filed: Jul. 16, 1996

(86) PCT No.: PCT/IL96/00050

§ 371 Date: Apr. 2, 1998

§ 102(e) Date: Apr. 2, 1998

(87) PCT Pub. No.: WO97/03609

PCT Pub. Date: Feb. 6, 1997

(30) Foreign Application Priority Data

Jul. 16, 1995 (IL) ........................................ 114610

(51) Int. Cl.[7] ........................................ A61B 6/00
(52) U.S. Cl. ........................ 600/427; 600/411; 600/439; 600/461; 606/130
(58) Field of Search ................................. 600/407, 427, 600/417, 429, 439, 446, 459, 461; 128/899, 916; 606/130

(56) References Cited

U.S. PATENT DOCUMENTS

| 4,407,294 | * | 10/1983 | Vilkomerson . |
| 4,671,292 | * | 6/1987 | Matzuk . |
| 4,839,836 | | 6/1989 | Fonsalas . |
| 4,899,756 | | 2/1990 | Sonek . |
| 4,911,173 | | 3/1990 | Terwilliger . |
| 4,945,305 | | 7/1990 | Blood . |
| 5,078,140 | | 1/1992 | Kwoh . |
| 5,095,910 | * | 3/1992 | Powers . |
| 5,309,913 | * | 5/1994 | Kormos et al. . |
| 5,526,812 | * | 6/1996 | Dumoulin et al. . |
| 5,529,070 | * | 6/1996 | Augustine et al. . |
| 5,558,091 | * | 9/1996 | Acker et al. . |
| 5,608,849 | * | 3/1997 | King, Jr. . |
| 5,611,345 | * | 3/1997 | Hibbeln . |
| 5,647,373 | | 7/1997 | Paltieli . |
| 5,662,111 | * | 9/1997 | Cosman . |
| 5,701,898 | * | 12/1997 | Adam et al. . |
| 5,758,650 | * | 6/1998 | Miller et al. . |
| 5,792,147 | * | 8/1998 | Evans et al. . |
| 5,810,008 | * | 9/1998 | Dekel et al. . |
| 5,817,022 | * | 10/1998 | Vesely . |
| 5,829,439 | * | 11/1998 | Yokosawa et al. . |
| 5,829,444 | * | 11/1998 | Ferre et al. . |
| 5,920,395 | * | 7/1999 | Schulz . |

FOREIGN PATENT DOCUMENTS 0427358 5/1991 (EP) .

* cited by examiner

*Primary Examiner*—Marvin M. Lateef
*Assistant Examiner*—Shawna J Shaw
(74) *Attorney, Agent, or Firm*—Kenyon & Kenyon

(57) ABSTRACT

A method for free-hand directing of a needle towards a target located in a body volume. The method includes the steps of producing an image of the target and the body volume, transmitting the image by means of an imaging detector to a display screen which communicates with a position sensing controller, sensing spatial orientation data of the imaging detector with respect to a reference, transmitting the spatial orientation data onto the display screen, placing the needle with a point thereof substantially pointing at the target sensing spatial orientation data of the needle with respect to the reference, transmitting the spatial orientation data of the needle to the position sensing controller, causing the position sensing controller, based on the spatial orientation data of the imaging detector and of the needle, to indicate on the display screen a trajectory of the needle point, and inserting the needle into the body volume towards the target in accordance with the trajectory indicated on the display screen.

37 Claims, 12 Drawing Sheets

FREE-HAND AIMING OF A NEEDLE GUIDE

FIELD OF THE INVENTION

The present invention relates to apparatus for performing needle biopsy, aspiration or injection by computer-aided controlled movement of a medical needle as it penetrates the body guided by an ultrasound or other imaging device.

BACKGROUND INFORMATION

Recently ultrasound diagnosis and therapy have become widely used, and many surgical procedures have been replaced by gentler and less time consuming invasive needle therapy to the benefit of the patient. Inter alia, ultrasonic imaging of maternal and fetal tissues has greatly facilitated prenatal diagnosis and treatment, and ultrasound imaging devices greatly assist the physician in properly positioning a biopsy needle to perform amniocentesis, cordocentesis and trans-abdominal chorionic sampling.

There are many different biopsy techniques and needles, and the needle depends on the type of patient and the target organ. The method most widely used today is the "free hand" technique, whereby the transducer is placed at a certain distance from the entry site of the needle and the needle is manipulated with one hand. This technique requires considerable skill and frequently repeated punctures, unless the target is relatively large or located superficially. For these reasons and because manipulation of the needle as guided by an ultrasound image generally requires both hands of the physician, much effort has been made to design and provide automatic devices for guiding the needle as directed by the ultrasound beam.

Early developed devices include a needle attached to an ultrasound transducer housing, the needle being spaced from and articulated with respect to the transducer. Such devices help the physician to manually direct the needle onto the desired biopsy location and to insert it to the required depth. Such devices are, for instance, described in U.S. Pat. No. 4,899,756, issued to Sonec, and U.S. Pat. No. 4,911,173, issued to Terwillinger. While all of these devices provided some movement of the needle guide and needle relative to the transducer, the physician is nevertheless significantly hampered in positioning the needle prior to and during insertion, as well as in re-positioning the transducer once the needle is inserted into the body.

Other commonly used devices include a transducer and a coaxial needle guide for manually positioning and inserting a needle. While these devices allow rapid and convenient guided biopsy, they have several significant drawbacks: 1) The transducer must be placed directly over the lesion, thereby requiring its sterilization or its draping by a sterile covering. 2) The physician is forced to hold the transducer in one hand while using the other for sterilizing and anesthetizing the biopsy site. 3) After inserting the needle, the transducer must be held by an assistant or must be removed while the needle is maneuvered. 4) Multiple passes may necessitate re-positioning of the transducer and re-insertion of the needle. 5) The existing needle guides may make it difficult to enter some superficial lesions. 6) Most transducers are flat, straight and relatively large, making some costal and subcostal approaches difficult.

A completely automatic apparatus for computer controlled stereotactic brain surgery is described in U.S. Pat. No. 5,078,140, issued to Kwoh. This apparatus suffers from the drawback that the needle or needle guide is integrally connected to the apparatus, thereby not permitting the physician to choose the most suitable trajectory of the needle towards the target. In addition, the apparatus is highly complicated, expensive and has to be calibrated for every operation.

Another device is an ultrasound directed needle guide, developed by the present Applicant, and disclosed in Israel Patent Application 107,523. It includes an ultrasound transducer and a needle, guide which holds a syringe and needle. Both the transducer and the needle guide are each attached to a universally movable arm such that each may be placed on a patient's body in any desired position. The arms are vertically movable along a vertical post and are provided with direction sensors configured to signal the position of the attached instruments to computer means. The transducer transmits the image of the target to an imaging device which in turn transmits the information to the computer means which is programmed to indicate the angular direction of the needle guide onto the target and to direct the physician to place the needle in the correct position and direction on the patient's body.

SUMMARY OF THE INVENTION

The present invention seeks, inter alia, to improve the articulated arm system disclosed in applicant's above mentioned Israel Patent Application 107,523. The present invention does away with the articulated arm and provides an improved "free-hand" technique for using the transducer and needle. The transducer is used to project on a computer screen an image of a body portion to be treated, thereby permitting a physician to obtain on the screen the preferred needle trajectory as well as the actual position of the needle guide, inserted needle and needle tip. The physician may then correct the actual trajectory in accordance with the displayed information.

Optionally, the target in the body portion to be treated may be selected and marked by the physician, such as with a cursor or other selection device. In case the needle point does not lie in the plane of the target image, the physician either changes the position of the needle or rotates the imaging source or detector so as to obtain the coinciding plane on the display screen.

Unlike the prior art, the present invention provides a system for multiple, daily use by any physician who does not need to be specially skilled in the art.

In the present invention, the image may be produced by any known imaging apparatus, such as ultrasound, computerized tomography (CT) or X-ray, which will permit positioning of the ultrasound transducer or other imaging detector at a distance from the actual entry site, thereby permitting the physician to place the needle in an optimal position.

It is noted that throughout the specification and claims the term "needle" encompasses any invasive device or tool and the term "needle guide" encompasses any device for holding and guiding a needle (or invasive device or tool) as well as a needle (or invasive device or tool) with an integrated electronic system. The term "orientation" encompasses spatial position information with respect to six degrees of freedom, such as in a Cartesian system, position along any of three mutually perpendicular axes and angular rotation about any of the axes. The terms "orientation" and "position" are used interchangeably.

The present invention may use a variety of apparatus for sensing the orientation of the transducer and needle. One preferred embodiment of apparatus for defining the position of the ultrasound transducer with wireless transmission includes mounting three small battery-operated infrared ultrasonic transponders on the ultrasound transducer in triangular alignment, each transponder having a different triggering code. A position sensing device is provided with three spaced-apart infrared ultrasonic transceivers which emit coded infrared signals to the respective transponder on the transducer and which receive ultrasonic responses from the respective transponder. The received signals provide triangulation information for the controller to calculate the exact position of the transducer in three-dimensional space.

A position sensing unit for the needle may work in a similar manner. The position sensing unit is provided with at least two transceivers configured to transmit wireless coded infrared signals to at least two transponders mounted on the needle or needle guide which issue coded signals back to the transceivers for calculating the needle position and direction, and to transmit the data to the computing device for display on the screen.

In another embodiment, both the transducer and the needle are provided with transmitters which continuously emit signals which are received by separate receivers. The received signals are transmitted to a computer for computing the spatial orientation of the transducer and needle.

In yet another embodiment, the position and orientation control system is based on magnetic field sensors, such as described in U.S. Pat. No. 4,945,305 to Boyd, the disclosure of which is incorporated herein by reference. The system preferably includes a personal computer, magnetic field sensors, a magnetic transmitter, a magnetic receiver attached to an ultrasound probe, and a magnetic receiver attached to a needle. A display screen shows an exact real-time ultrasound image of the targeted area, and the needle and the needle trajectory are shown in accordance with a color coded scheme. The color coded scheme indicates whether the needle and the trajectory lie in the ultrasound plane or parallel thereto or intersect therewith.

It is appreciated that the orientation sensors of the transducer and the needle may comprise many other types of sensing devices. For example, the sensors may comprise clusters of accelerometers which provide spatial orientation data signals, such as described in U.S. Pat. No. 4,839,836, the disclosure of which is incorporated herein by reference.

The ability of the present invention to provide marking of the target enables the physician to mark the target, move on to other tasks, and then return to the target at some later time, whether a needle is eventually inserted into the target or not. This auxiliary feature frees the physician to do other tasks in the middle of an ultrasound examination, for example, and still be able to manipulate the ultrasound transducer to return to the target.

There is thus provided in accordance with a preferred embodiment of the present invention, a method for freehand directing of a needle towards a target located in a body volume, the method including the steps of producing an image of the target and the body volume, transmitting the image by means of an imaging detector to a display screen which communicates with a position sensing controller, sensing spatial orientation data of the imaging detector with respect to a reference, transmitting the spatial orientation data of the imaging detector to the position sensing controller, displaying the spatial orientation data onto the display screen, placing the needle with a point thereof substantially pointing at the target, sensing spatial orientation data of the needle with respect to the reference, transmitting the spatial orientation data of the needle to the position sensing controller, causing the position sensing controller, based on the spatial orientation data of the imaging detector and of the needle, to indicate on the display screen a trajectory of the needle point, and inserting the needle into the body volume towards the target in accordance with the trajectory indicated on the display screen.

In accordance with a preferred embodiment of the present invention, the method further includes the step of indicating on the display screen an actual progressive motion of the needle towards the target.

Additionally in accordance with a preferred embodiment of the present invention, the method further includes the step of indicating on the display screen a deviation of the needle from the trajectory.

Further in accordance with a preferred embodiment of the present invention, the method further includes the step of adjusting a planar direction of the image so as to cause it to coincide with the position of the needle point entering the target.

Still further in accordance with a preferred embodiment of the present invention, the method further includes the step of indicating to the position sensing controller the position of the target by marking the target on the display screen.

In accordance with a preferred embodiment of the present invention, the steps of transmitting the spatial orientation data of the imaging detector and the needle to the position sensing controller are performed by means of wired communication.

Additionally the steps of transmitting the spatial orientation data of the imaging detector and the needle to the position sensing controller are performed by means of wireless communication.

Further in accordance with a preferred embodiment of the present invention, the position sensing controller indicate on the display screen a two-dimensional trajectory of the needle point.

Still further in accordance with a preferred embodiment of the present invention, the position sensing controller indicate on the display screen a three-dimensional trajectory of the needle point.

In accordance with a preferred embodiment of the present invention, the method further includes the step of displaying the spatial orientation data of the needle onto the display screen.

Additionally in accordance with a preferred embodiment of the present invention, the step of producing an image is performed by ultrasound imaging equipment.

Further in accordance with a preferred embodiment of the present invention, the step of producing an image is performed by X-Ray equipment.

Still further in accordance with a preferred embodiment of the present invention, the step of producing an image is performed by computerized tomography equipment.

In accordance with a preferred embodiment of the present invention, the step of producing an image is performed by magnetic resonance imaging equipment.

There is also provided in accordance with a preferred embodiment of the present invention, apparatus for freehand directing of a needle having a point towards a target located in a body volume, the needle being manipulated only by a hand of the user, the apparatus including a position sensing controller which communicates with a display screen, imaging apparatus for producing an image of the body volume and the target, an imaging detector for transmitting the image onto the display screen, a probe orientation sensor for sensing spatial orientation data of the imaging detector with respect to a reference, and a needle orientation sensor for sensing spatial orientation data of the needle with respect to the target, whereby the position sensing controller, based on the spatial orientation data of the imaging detector and of the needle, indicates on the display screen a trajectory from the needle point into the target.

In accordance with a preferred embodiment of the present invention, the imaging apparatus is ultrasound imaging apparatus and the imaging detector is an ultrasound transducer.

Additionally in accordance with a preferred embodiment of the present invention, the probe orientation sensor communicates with the position sensing controller via a triggering code.

Further in accordance with a preferred embodiment of the present invention, the needle orientation sensor communicates with the position sensing controller via a triggering code.

Still further in accordance with a preferred embodiment of the present invention, the probe orientation sensor and the needle orientation sensor are electro-optical sensors.

In accordance with a preferred embodiment of the present invention, the probe orientation sensor and the needle orientation sensor are magnetic sensors.

Additionally in accordance with a preferred embodiment of the present invention, there is provided a three-dimensional viewing device for three-dimensionally viewing the needle and the trajectory on the display screen.

BRIEF DESCRIPTION OF THE DRAWINGS

The present invention will be understood and appreciated more fully from the following detailed description, taken in conjunction with the drawings in which.

DETAILED DESCRIPTION OF THE DRAWINGS

Figure 1:
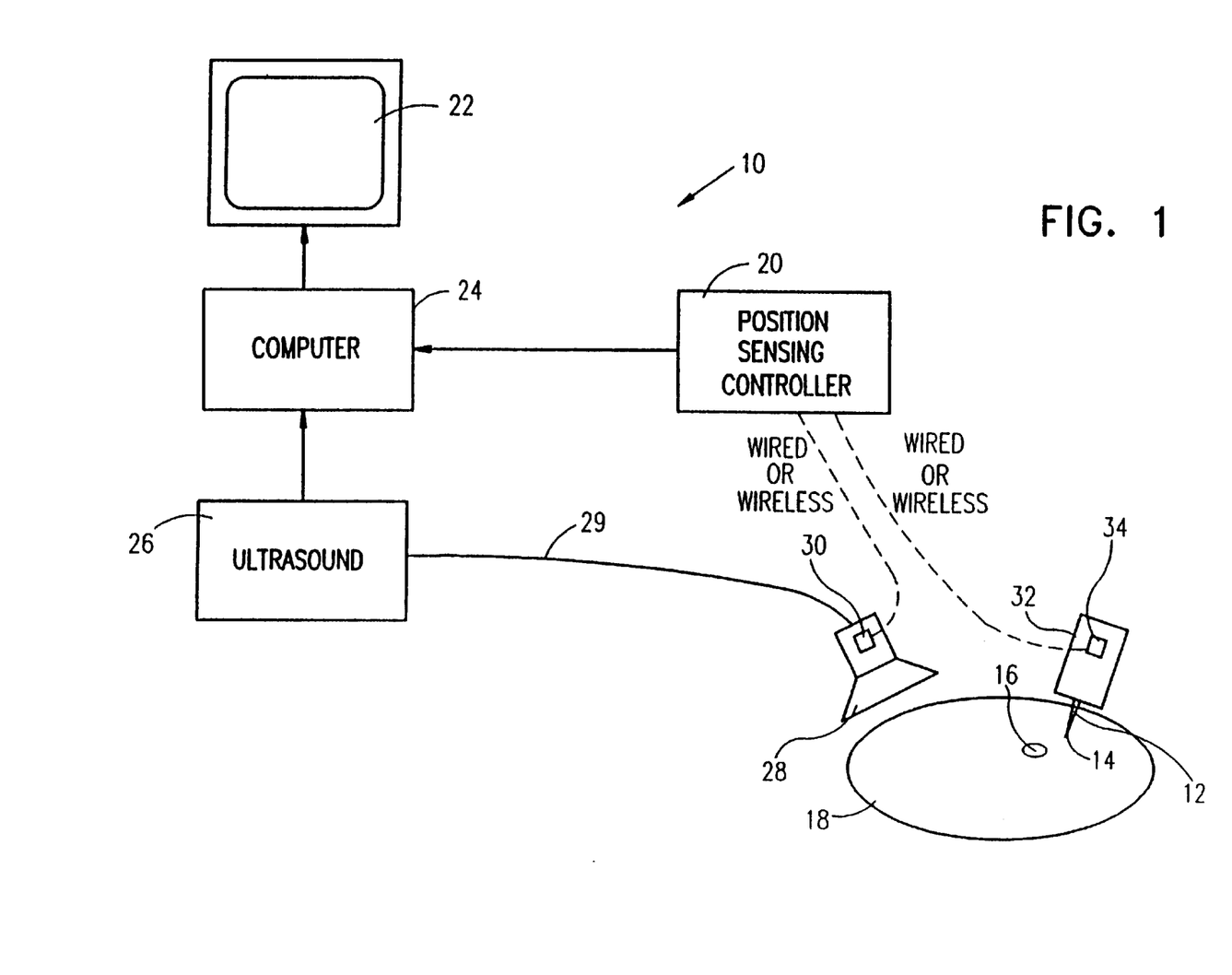
FIG. 1 is a simplified block diagram of apparatus, constructed and operative in accordance with a preferred embodiment of the present invention, for directing a needle having a point towards a target located in a body volume, and including an ultrasound imaging system.

Reference is now made to FIG. 1 which is a simplified block diagram of apparatus 10, constructed and operative in accordance with a preferred embodiment of the present invention, for directing a needle 12 having a point 14 towards a target 16 located in a body volume 18.

Apparatus 10 preferably includes a position sensing controller 20 which communicates with a display screen 22, preferably via a computer 24. Imaging apparatus, such as an ultrasound imaging system 26, is preferably provided for producing an image of target 16 and body volume 18 by directing ultrasound waves thereto. An imaging detector, such as an ultrasound probe 28, preferably communicates with system 26 such as by means of a cable 29, for transmitting the image onto display screen 22, preferably via computer 24. Unlike the prior art, probe 28 is not held or guided by articulated means, but is manipulated "free-hand".

Preferably disposed in probe 28 is a probe orientation sensor 30 for sensing spatial position data of probe 28 with respect to a reference, such as a given inertial reference origin. The position data is preferably displayed on display screen 22, and a user looking at display screen 22 can direct needle 12 towards target 16. Optionally, the user may indicate to position sensing controller 20 the position of target 16 by marking target 16 on display screen 22. This marking may be done by any convenient method, such as by a keyboard, mouse, joystick, thumb wheel or touch screen. An advantage of the option of marking the target 16 is described hereinbelow with reference to FIG. 7.

Needle 12 is preferably held fixed in a needle guide 32. Different embodiments of needles and needle guides will be described in further detail hereinbelow with reference to FIGS. 5, 6, 11, 12 and 13. Unlike the prior art, neither needle 12 nor needle guide 32 is held or guided by articulated means, but is manipulated "free-hand".

Preferably a needle orientation sensor 34 is disposed in needle guide 32, or alternatively needle 12, for sensing spatial orientation data of needle 12 with respect to the reference. Position sensing controller 20, based on the spatial orientation data of needle 12, indicates on display screen 22 a trajectory from needle point 14, the trajectory being an imaginary straight ray emanating from needle point 14 along the longitudinal axis of needle 12. Probe orientation sensor 30 and needle orientation sensor 34 may be in wired or wireless communication with position sensing controller 20.

Figure 2:
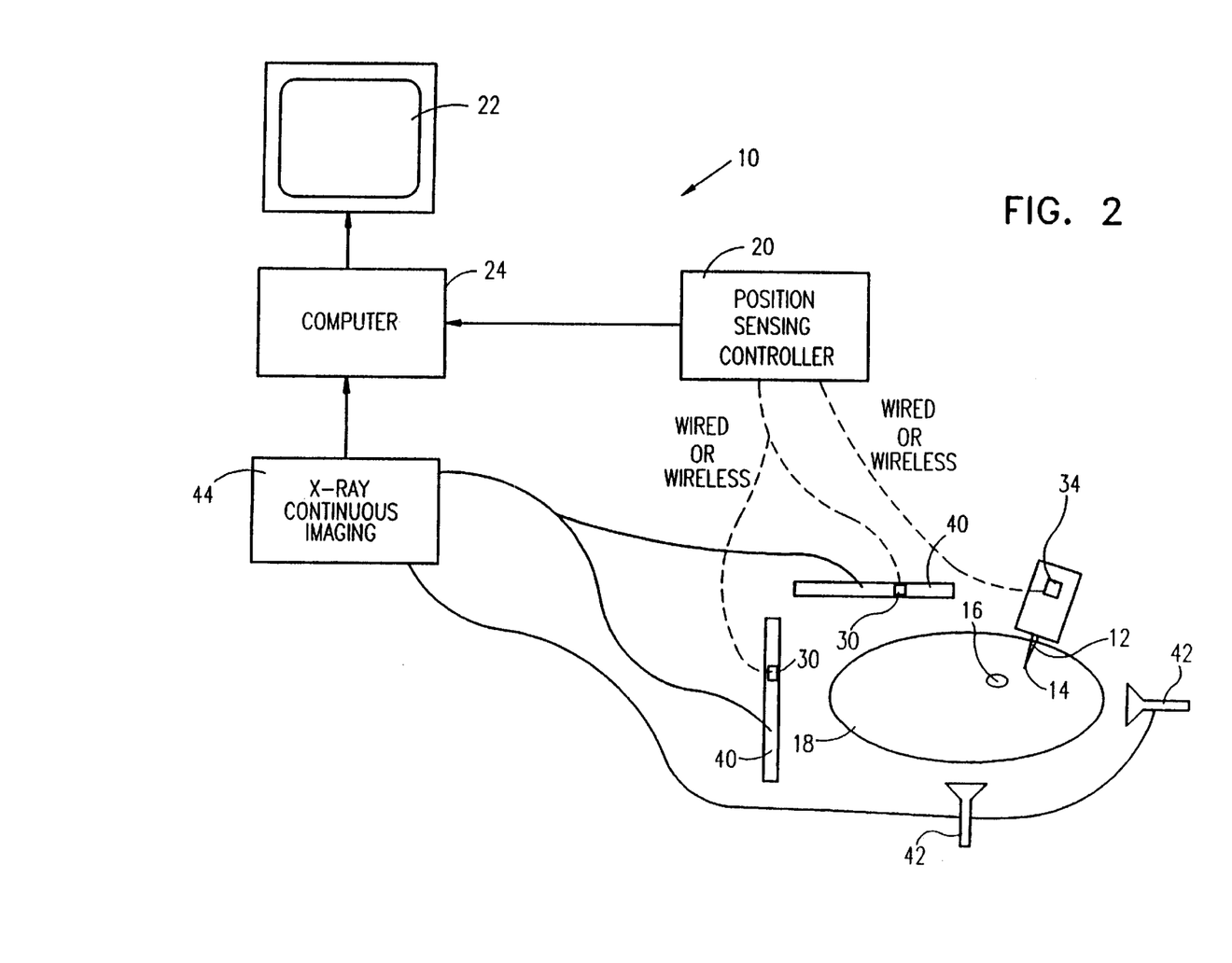
FIG. 2 is a simplified block diagram of apparatus, constructed and operative in accordance with another preferred embodiment of the present invention, for directing a needle having a point towards a target located in a body volume, and including an X-ray imaging system.
Figure 3:
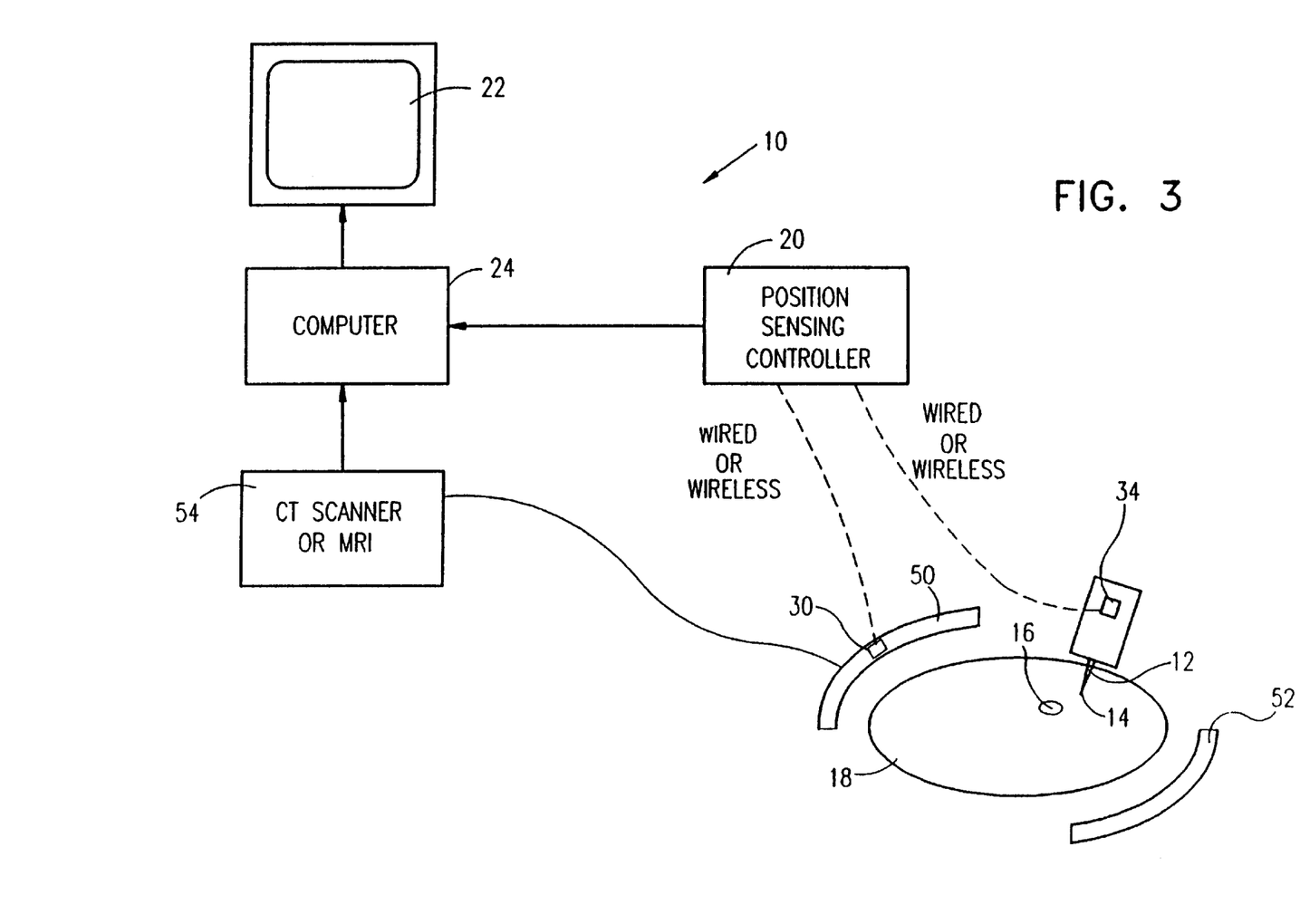
FIG. 3 is a simplified block diagram of apparatus, constructed and operative in accordance with yet another preferred embodiment of the present invention, for directing a needle having a point towards a target located in a body volume, and including a computerized tomography (CT) or magnetic resonance imaging (MRI) system.

Reference is now made to FIGS. 2 and 3 which illustrate further embodiments of apparatus 10, wherein the imaging detector and apparatus, instead of an ultrasound probe and system, respectively comprise one or more x-ray detectors 40, one or more x-ray radiation sources 42, and an x-ray continuous imaging system 44 (FIG. 2), and a CT or MRI detector 50, a CT or MRI radiation source 52, and a CT or MRI scanner system 54 (FIG. 3).

Figure 4:
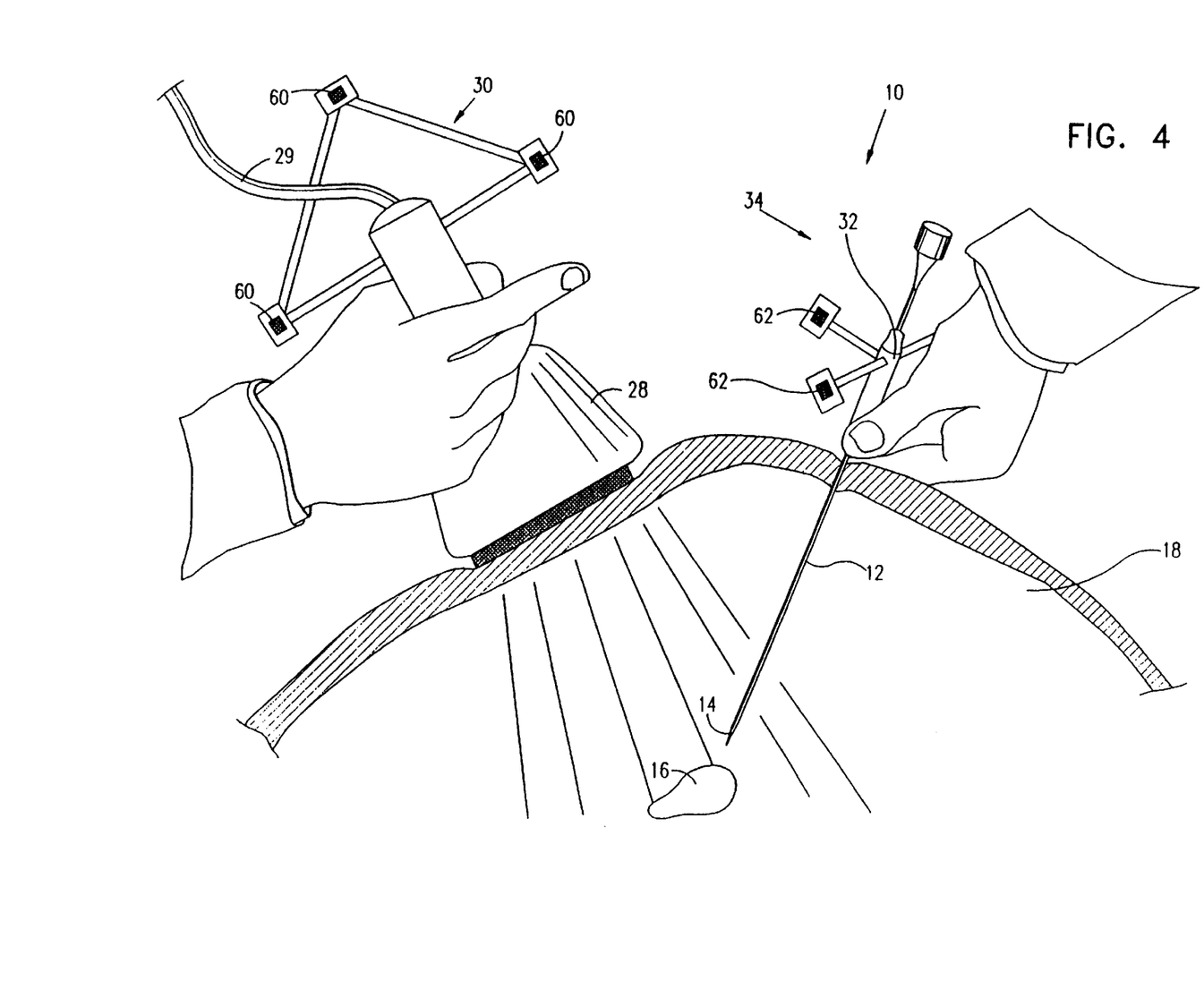
FIG. 4 is a simplified pictorial illustration of directing the point of the needle towards the target, in accordance with a preferred embodiment of the present invention, using an ultrasound transducer and a needle guide each provided with three spaced-apart transponders.

Reference is now made to FIG. 4 which illustrates directing point 14 of needle 12 towards target 16, in accordance with a preferred embodiment of the present invention, using ultrasound probe 28 and needle guide 32. It is appreciated that needle guide 32 may carry a syringe (not shown) for injection or tissue examination. In the illustrated embodiment, probe orientation sensor 30 and needle orientation sensor 34 each comprise an array of three spaced-apart transponders 60 and 62, respectively, in triangular alignment. Transponders 60 and 62 are preferably electro-optical sensors which operate with infrared or visible light. Transponders 60 and 62 preferably respond to coded signals emitted by probe orientation sensor 30 and needle orientation sensor 34, respectively. Alternatively, only two responders 62 may be provided in line with a vertical axis of needle 12 to define the position of needle guide 32, there being no need for rotary adjustment of needle 12.

While three transponders are illustrated in FIG. 4, it is appreciated that all three transponders may be alternatively packaged as one transponder unit.

Figure 5:
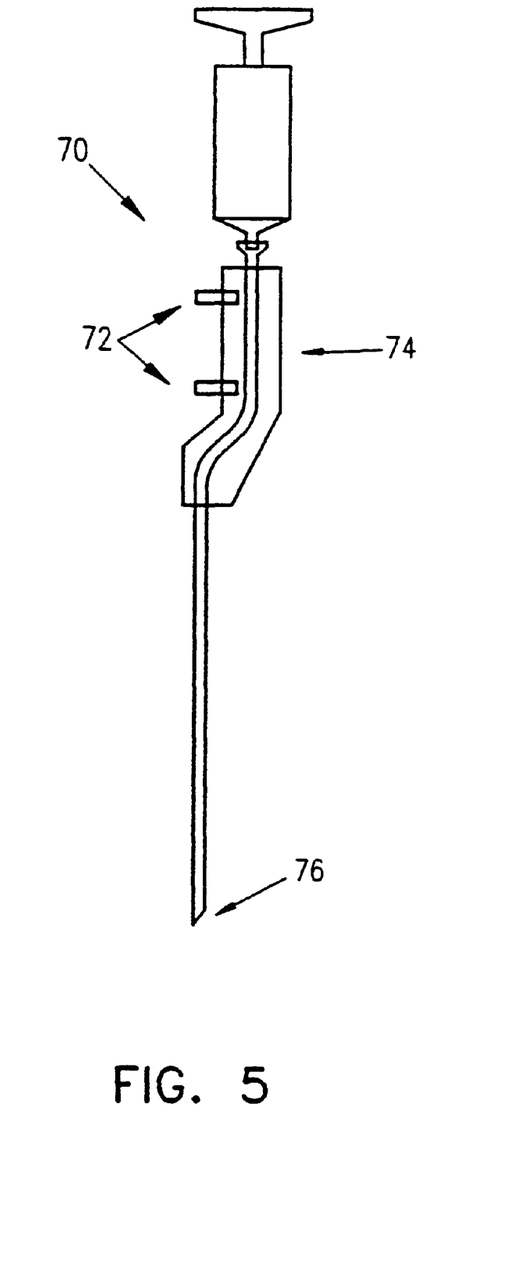
FIG. 5 is a simplified illustration of a needle provided with two coaxially mounted emitters or transponders.

It is appreciated that needle orientation sensors may be mounted on the needle in a variety of manners. Reference is now made to FIG. 5 which illustrates a needle 70 provided with two coaxially mounted emitters or transponders 72. Transponders 72 may be mounted on the body of needle 70 by bending needle 70 into an approximate S-shape and attaching transponders 72 to an upper portion 74 of the S-shape. Since the distance of a needle point 76 from the transponders 72 is known, it is possible to compute and to show the depth of entry of needle 70 on display screen 22 (not shown).

Figure 6:
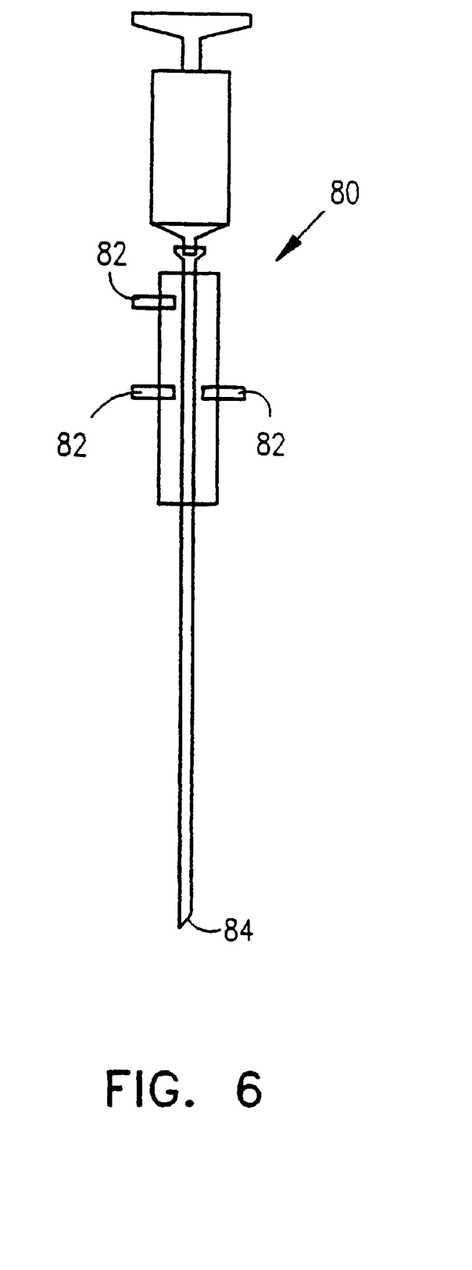
FIG. 6 is a simplified illustration of a needle provided with three emitters or transponders.

Reference is now made to FIG. 6 which illustrates a needle 80 provided with three emitters or transponders 82. Needle 80 is substantially straight, and transponders 82 are preferably fixedly attached to the body of needle 80 in a fixed relationship with a needle point 84, thereby making it possible to compute and to show the depth of entry of needle 80 on display screen 22 (not shown).

Figure 7:
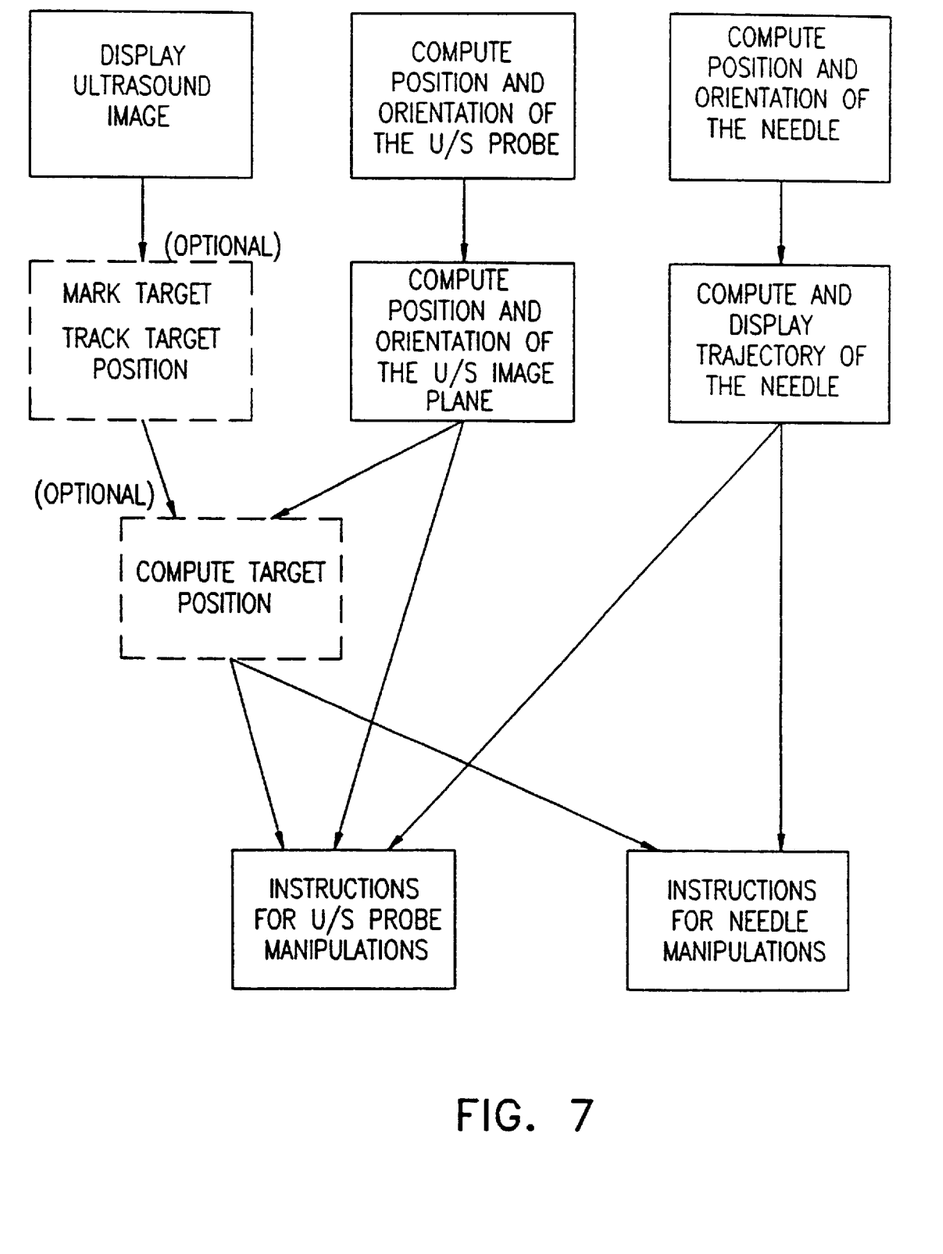
FIG. 7 is a simplified flow chart of a method for directing a needle having a point towards a target located in a body volume, in accordance with a preferred embodiment of the present invention, using an ultrasound imaging system.

Reference is now made to FIG. 7 which is a simplified flow chart of a method for directing needle point 14 towards target 16, in accordance with a preferred embodiment of the present invention, using ultrasound imaging system 26.

Ultrasound system 26 produces an image containing the target and this image is sent to and displayed on display screen 22. Computer 24 receives data from probe orientation sensor 30 and needle orientation sensor 34 and computes the position of both probe 28 and needle guide 32 in relation to an inertial reference. Computer 24 also computes position and orientation of the ultrasound image plane associated with probe 28. Since the two-dimensional projections of yaw, pitch and rotation of probe 28 appear on screen 22, the user can rotate probe 28 so as to place needle point 14 into the viewed plane.

Computer 24 will now compute the trajectory of needle 12, typically in accordance with well known geometric formulas. As stated above, the trajectory is an imaginary straight ray emanating from needle point 14 along the longitudinal axis of needle 12. The trajectory is displayed on screen 22, and the user may then insert needle 12 towards target 16, after having shifted needle guide 32, if necessary. The path of needle 12 during insertion is displayed on screen 22 and can be corrected in case of accidental deviation.

Optionally, the user may mark target 16 on screen 22 such as by means of a keyboard, mouse, joystick, thumb wheel or touch screen. After marking target 16, computer 24 can calculate the spatial position thereof and target 16 may then be tracked according to known tracking methods of the art, such as by tracking it in contrast with the ultrasound image.

The ability to track a target may be important in some situations when the target moves due to movement of the body organ in which it lies. By marking the target, the physician can be alerted to movement of the target and change the invasive procedure accordingly in order to precisely pierce the target with the needle.

The foregoing description is a generalized description of a preferred method for directing the needle to the target. A more detailed description of another preferred method will be described hereinbelow for the embodiment of FIG. 8.

Figure 8:
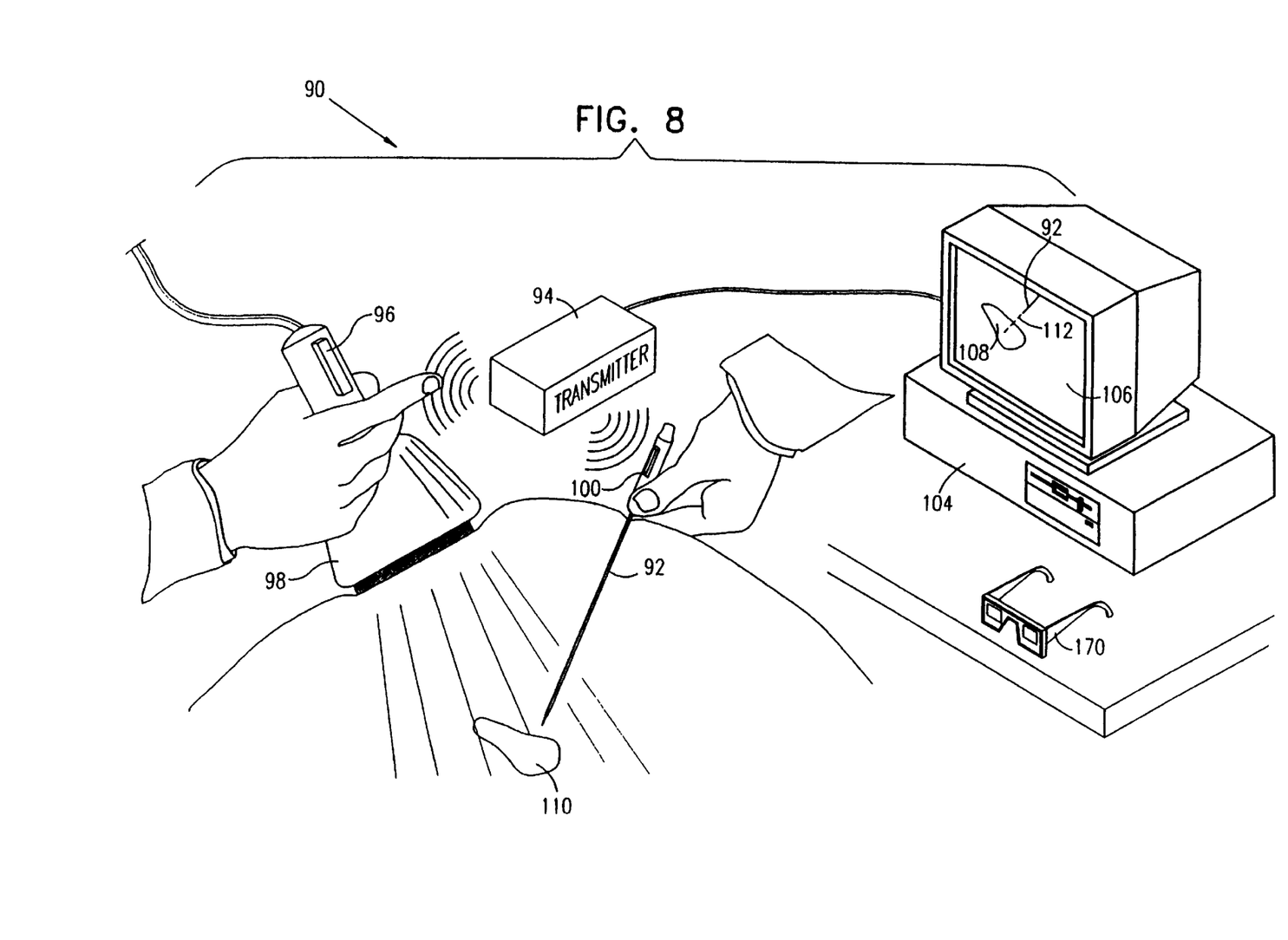
FIG. 8 is a simplified illustration of apparatus for free-hand directing of a needle, constructed and operative in accordance with yet another preferred embodiment of the present invention.

Reference is now made to FIG. 8 which illustrates apparatus 90 for free-hand directing of a needle 92, constructed and operative in accordance with yet another preferred embodiment of the present invention. Apparatus 90 preferably includes a magnetic field position and orientation sensing system, such as described in U.S. Pat. No. 4,945,305 to Blood. The magnetic system preferably includes a magnetic transmitter 94, a magnetic receiver 96 attached to an ultrasound probe 98. and a magnetic receiver 100 attached to needle 92. Apparatus 90 preferably includes a computer 104 with a display screen 106. Display screen 106 preferably displays an exact real-time ultrasound image 108 of a targeted area 110. Needle 92, in a preferred embodiment, is shown as a distinctly colored line, such as a blue line, even if needle 92 is outside the ultrasound image 108. The expected trajectory 112 of needle 92 is preferably displayed in accordance with a color scheme, so that a physician may quickly and easily discern the relation of the needle trajectory 112 with the plane of the ultrasound image 108. An example of such a color scheme is described hereinbelow with reference to FIGS. 9 and 10.

A three-dimensional viewing device 170, such as a three-dimensional eyeglasses device, may be provided for viewing needle 92 and trajectory 112 three-dimensionally. Alternatively, computer 104 may be provided with a three-dimensional imaging program for displaying three-dimensional images of needle 92 and trajectory 112 on display screen 106. Such a program may, for example, form the three-dimensional images by displaying consecutive two-dimensional images of the objects corresponding to views projected onto the left and right eyes.

Figure 9:
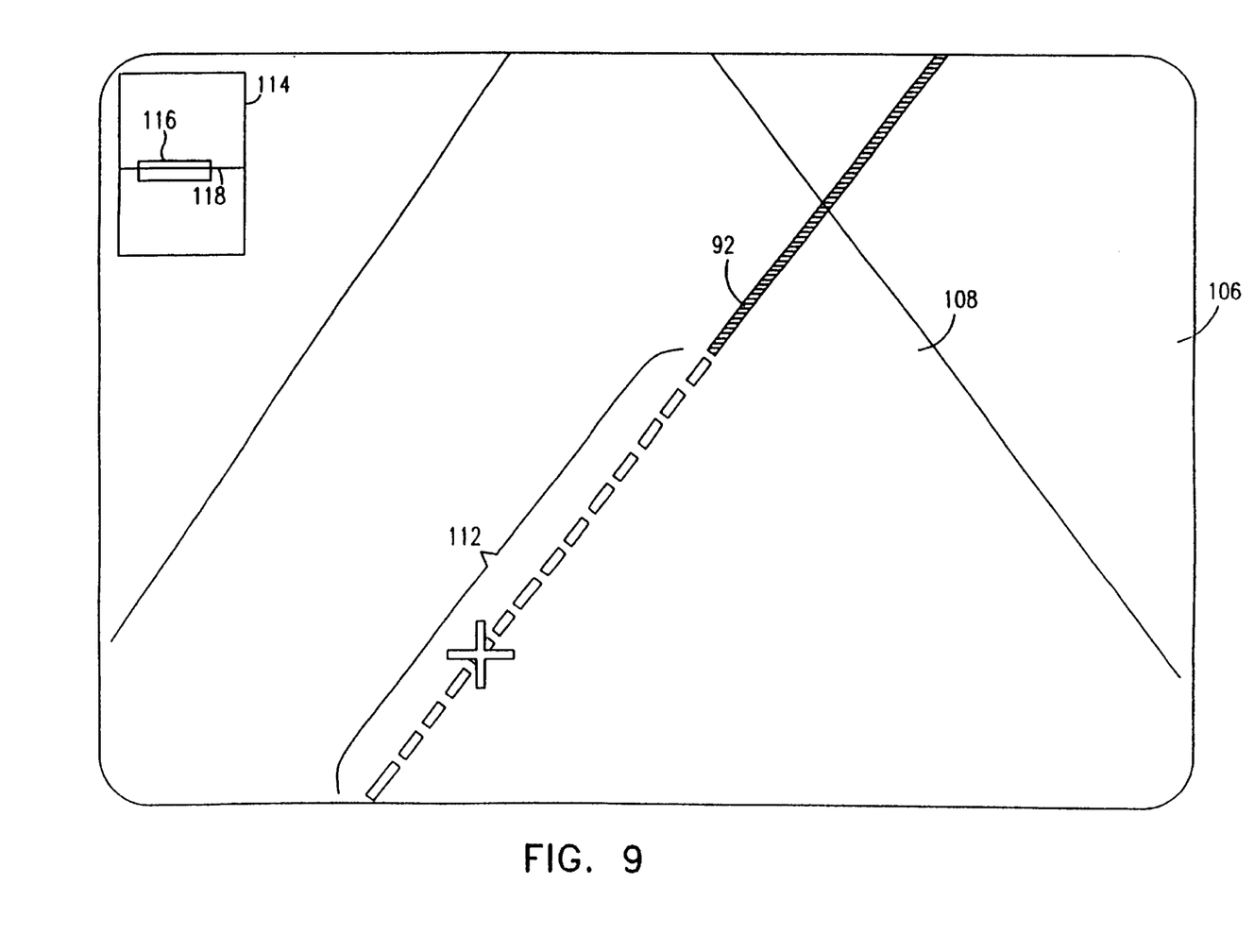
FIG. 9 is a simplified illustration of a computer screen displaying the needle and needle trajectory in the same plane as the ultrasound plane.
Figure 10:
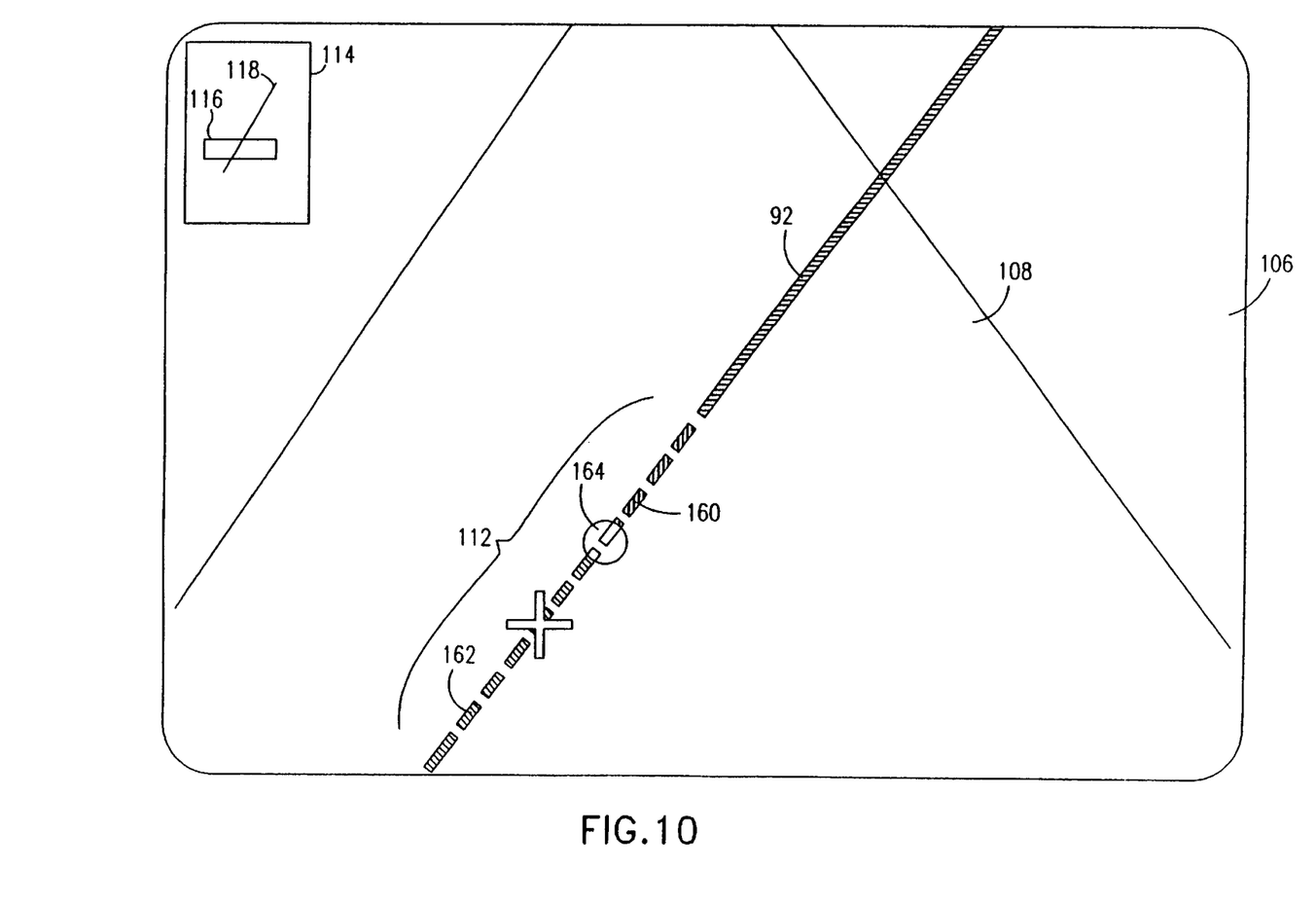
FIG. 10 is a simplified illustration of a computer screen displaying the needle and needle trajectory intersecting the ultrasound plane.

As seen in FIG. 9, if trajectory 112 and needle 92 both entirely lie within the ultrasound plane, then trajectory 112 is shown as a white dotted line. As seen in FIG. 10, if trajectory 112 intersects the ultrasound plane, a portion 160 of trajectory 112 which lies in front of the ultrasound plane is displayed as a red dotted line, a portion 162 behind the plane is displayed as a green dotted line, and an intersection point 164 is displayed as a white empty circle. It is appreciated that these colors are merely examples, and other color patterns may be employed.

It is noted that if trajectory 112 is entirely in front of (or behind) the ultrasound plane, i.e., it is either parallel to the plane or the intersection point is out of view, then the entire trajectory 112 is displayed as a red (or green, if behind the plane) dotted line.

The distances between the dots of the dotted line may visually indicate to the physician an approximate angle of attack of needle 92 with the ultrasound plane. The closer the dots, the more needle 92 is perpendicular to the ultrasound plane. The further the dots, the more parallel needle 92 is to the ultrasound plane.

In addition, display screen 106 may optionally display a window 114 intended to aid the physician in positioning and orienting probe 98 (not shown in FIGS. 9 and 10). Window 114 preferably contains a fixed rectangle 116, designating a top view of probe 98, and a movable line 118 showing the projection of needle 92 as seen from above. While rotating or otherwise aligning ultrasound probe 98, the physician can observe in window 114 how probe 98 and needle 92 relate to each other in space as seen from above. Conversely, the image of needle 92 may be fixed and rectangle 116 may show movement of ultrasound probe 98.

In FIG. 9, since needle 92 lies in the ultrasound image plane, line 118 crosses horizontally through rectangle 116. In FIG. 10, since needle 92 intersects the ultrasound image plane, line 118 pierces rectangle 116 at an angle thereto.

If the physician chooses to insert needle 92 so that it lies entirely within the ultrasound plane, as shown in FIG. 9 for example, then the procedure is performed according to the following steps:
1. Select the needle insertion point.
2. Position the needle tip on the body at the point of insertion. Orient needle 92 such that the expected trajectory 112 crosses the target.
3. Rotate ultrasound probe 98 so that the ultrasound plane contains both the target and the whole of the needle and its expected trajectory. Once such aligned, the expected trajectory is shown in white. The rotation of probe 98 may be optionally observed in window 114.
4. Insert needle 92, making sure that it stays in the ultrasound plane, i.e., its displayed image remains white. When the display indicates that needle 92 has entered the ultrasound image (i.e., the blue solid line enters the image), observe needle 92 as imaged directly in the ultrasound image.
5. When approaching the target, take extra caution to observe the actual needle 92 and verify.
6. Insert needle 92 into the target if the orientations of the needle tip and target are verified.

If in-plane insertion is impossible in the specific procedure, or if the physician chooses to insert needle 92 so that it does not lie entirely within the plane of the ultrasound, the method is performed according to the following steps:
1. Select the needle insertion point.
2. Position the needle tip on the body at the point of insertion. Orient needle 92 such that the expected trajectory crosses the target, and that the white circle is on the target. This means that the trajectory crosses the ultrasound plane exactly at the target.
3. Insert needle 92.
4. Verify the actual position of the needle 92 as follows:
a) Change the orientation of ultrasound probe 98, until the white circle meets the tip of the blue solid line.
b) Observe the actual needle tip, as shown in the ultrasound image.
c) Once verified, return ultrasound probe 98 to the original position in accordance with step 2.
5. If at the verification step 4, deviation of the needle is observed, (the needle tip is away from the tip of the blue line), mark the actual needle tip. The computer will calculate a corrected trajectory, taking into account the observed deviation. The blue line representing needle 92 and the expected trajectory 112 will be redrawn according to the calculated correction.
6. When approaching the target, take extra caution to observe the actual needle and verify.
7. Insert needle 92 into the target if the orientations of the needle tip and target are verified.

Figure 11:
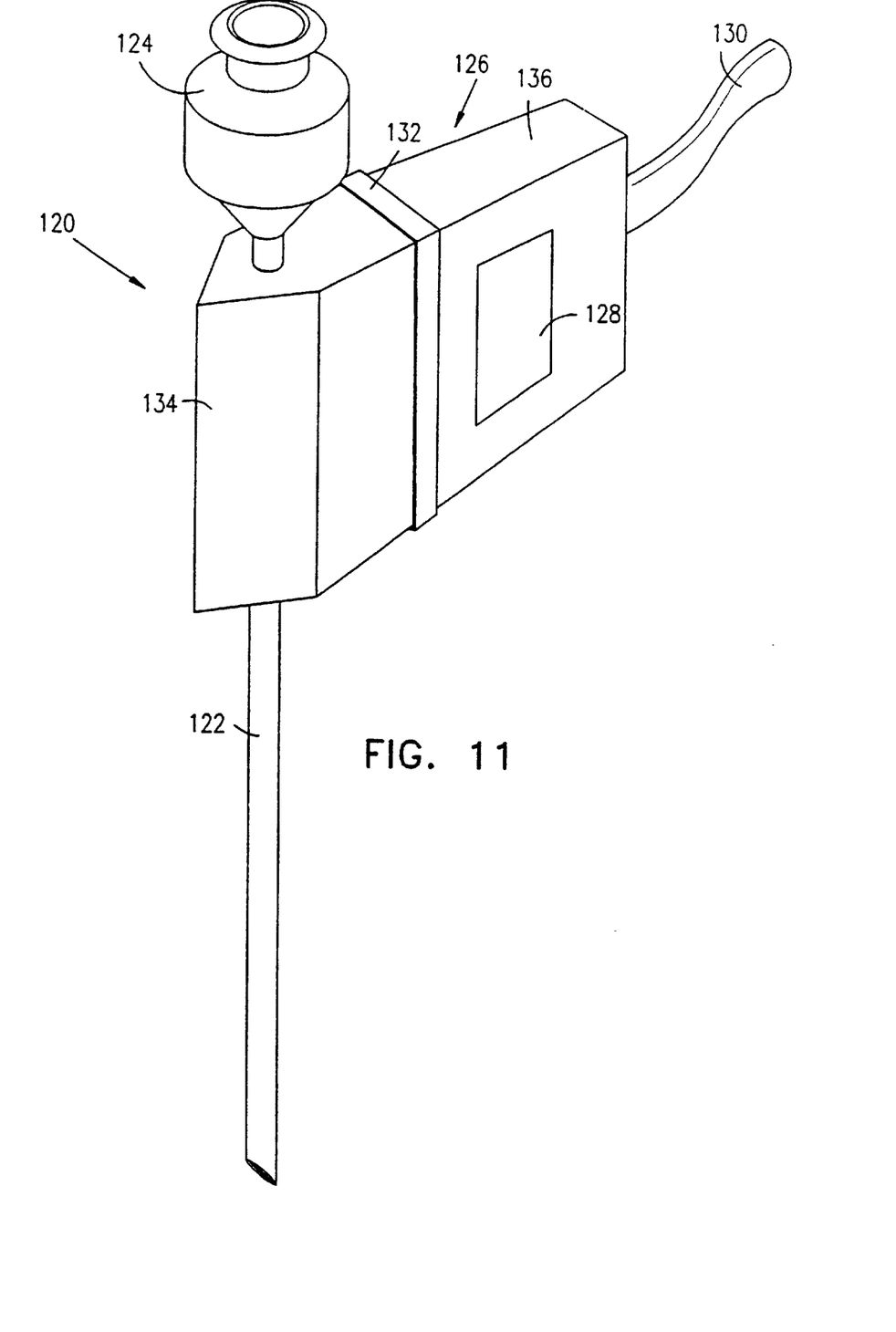
FIGS. 11, 12 and 13 are simplified illustrations of needle apparatus with a needle orientation sensor, constructed and operative in accordance with three preferred embodiments of the present invention.
Figure 12:
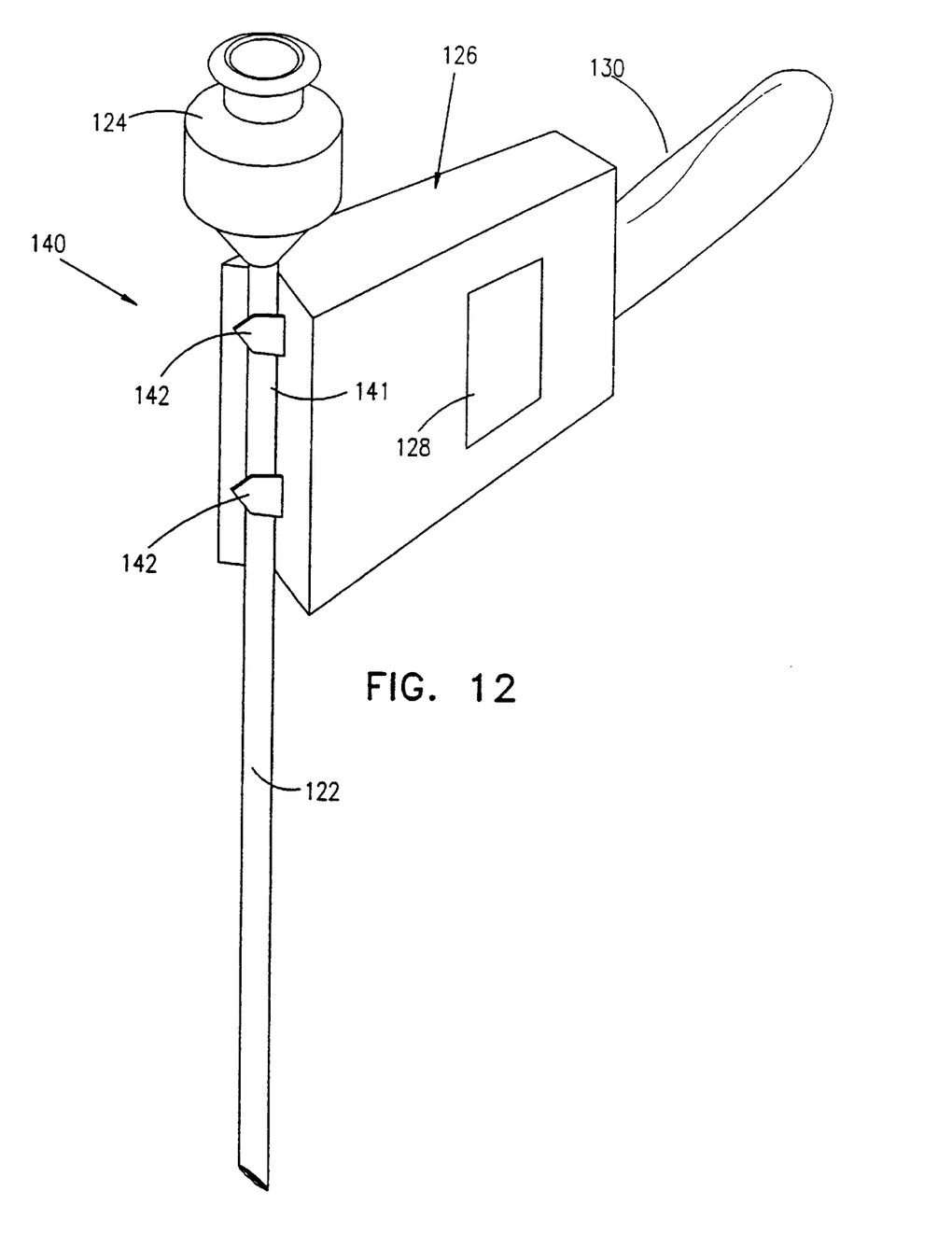
Figure 13:
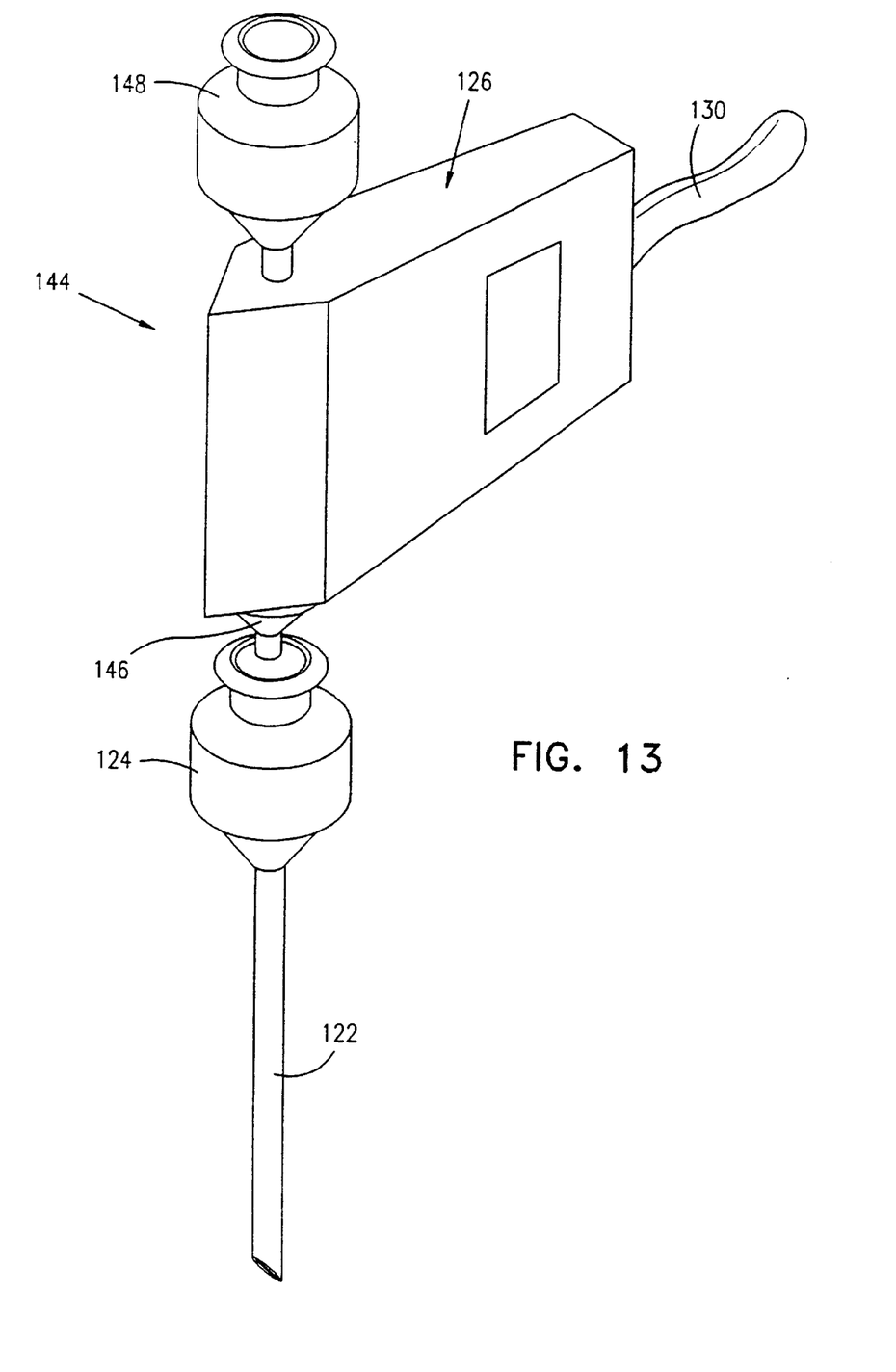

Reference is now made to FIGS. 11, 12 and 13 which are simplified illustrations of needle apparatus with a needle orientation sensor, constructed and operative in accordance with three preferred embodiments of the present invention.

In FIG. 11, there is shown needle apparatus 120 which preferably includes a needle 122 and a connector 124, preferably standard, for connection to a sampling device, such as syringe or other similar device (not shown). Apparatus 120 preferably further includes a body 126 on which is mounted a needle orientation sensor 128 for use with an orientation and position system, and an optional electric cable 130 for connecting sensor 128 with external circuitry (not shown). Sensor 128 is preferably embedded in body 126.

Optionally, body 126 may comprise two portions 134 and 136, joined together by a fastener 132. Portion 134 is preferably permanently attached to the disposable invasive needle 122, and portion 136 includes sensor 128 and optional cable 130, portion 136 being reusable and sterilizable before each use.

Reference is now made to FIG. 12 which illustrates needle apparatus 140, constructed and operative in accordance with another preferred embodiment of the present invention. Apparatus 140 is preferably substantially identical to needle apparatus 120 of FIG. 11. In needle apparatus 140, needle 122 is preferably fixed to a groove 141 formed in body 126 by means of one or more clips 142. Typically needle 122 cannot be removed from body 126 without breaking clips 142.

Reference is now made to FIG. 13 which illustrates needle apparatus 144, constructed and operative in accordance with yet another preferred embodiment of the present invention. Apparatus 144 is preferably substantially identical to needle apparatus 120 of FIG. 11, except that connector 124 of needle 122 is preferably attached to body 126 via a mating connector 146. An additional connector 148 is preferably in fluid communication with needle 122, and is mounted on body 126. Connector 148 may be used to connect apparatus 144 with a sampling device, such as a syringe or other similar device (not shown).

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited by what has been particularly shown and described hereinabove. Rather the scope of the present invention is defined only by the claims which follow.

What is claimed is:
1. A method for free-hand directing of a needle towards a target located in a body volume, the method comprising the steps of:
producing an image of said target and said body volume from an imaging detector;
transmitting said image produced by said imaging detector to a display screen which communicates with a position sensing controller;
sensing spatial orientation data of said imaging detector with respect to a reference;
transmitting said spatial orientation data of said imaging detector to said position sensing controller;
determining the position of said image in accordance with said spatial orientation data of said imaging detector;
placing said needle with at least a portion thereof substantially pointing at said target;
sensing spatial orientation data of said needle with respect to said reference;

transmitting said spatial orientation data of said needle to said position sensing controller;

causing said position sensing controller, based on said spatial orientation data of said imaging detector and of said needle, to indicate on said display screen at least one of the trajectory or the position of at least a portion of said needle with respect to said displayed image of said body volume.

2. The method according to claim 1 and further comprising the step of indicating on said display screen an actual progressive motion of said needle towards said target.

3. The method according to claim 1 and further comprising the step of indicating on said display screen a deviation of said needle from said trajectory.

4. The method according to claim 1 and further comprising the step of adjusting a planar direction of the image so as to cause it to coincide with the position of the needle point entering the target.

5. The method according to claim 1 and further comprising the step of indicating to said position sensing controller the position of said target by marking said target on said display screen.

6. The method according to claim 1 wherein said steps of transmitting said spatial orientation data of said imaging detector and said needle to said position sensing controller are performed by means of wired communication.

7. The method according to claim 1 wherein said steps of transmitting said spatial orientation data of said imaging detector and said needle to said position sensing controller are performed by means of wireless communication.

8. The method according to claim 1 wherein said position sensing controller indicates on said display screen a two-dimensional trajectory of said needle point.

9. The method according to claim 1 wherein said position sensing controller indicates on said display screen a three-dimensional trajectory of said needle point.

10. The method according to claim 1 and further comprising the step of displaying said spatial orientation data of said needle onto said display screen.

11. The method according to claim 1 wherein said step of producing an image is performed by ultrasound imaging equipment.

12. The method according to claim 1, wherein said step of producing an image is performed by X-Ray equipment.

13. The method according to claim 1, wherein said step of producing an image is performed by computerized tomography equipment.

14. The method according to claim 1, wherein said step of producing an image is performed by magnetic resonance imaging equipment.

15. The method of claim 1, additionally comprising, inserting said needle into said body volume in accordance with said position or said trajectory of said at least a portion of said needle indicated on said display screen.

16. The method of claim 1, wherein said at least a portion of said needle includes a predetermined point along said needle.

17. The method of claim 1, wherein said at least a portion of said needle includes the tip of said needle.

18. The method of claim 1, wherein said at least a portion of said needle includes at least substantially all of said needle.

19. Apparatus for free-hand directing of a needle towards a target located in a body volume, said needle being manipulated only by a hand of a user, said apparatus comprising:

a position sensing controller which communicates with a display screen;

an imaging apparatus for producing an image of said body volume and said target;

an imaging detector for transmitting said image onto said display screen;

a probe orientation sensor attached to said imaging detector for sensing spatial orientation data of said imaging detector with respect to a reference; and a needle orientation sensor attached to said needle for sensing spatial orientation data of said needle with respect to said reference; and said position sensing controller configured for determining the position of said displayed image from said spatial orientation data of said imaging detector and configured for indicating on said display screen at least one of the trajectory or the position of at least a portion of said needle with respect to said displayed image of said body volume, based on said spatial orientation data of said imaging detector and of said needle.

20. Apparatus according to claim 19 wherein said imaging apparatus is ultrasound imaging apparatus and said imaging detector is an ultrasound transducer.

21. Apparatus according to claim 19 wherein said probe orientation sensor communicates with said position sensing controller via a triggering code.

22. Apparatus according to claim 19 wherein said needle orientation sensor communicates with said position sensing controller via a triggering code.

23. Apparatus according to claim 19, wherein said probe orientation sensor and said needle orientation sensor are electro-optical sensors.

24. Apparatus according to claim 19, wherein said probe orientation sensor and said needle orientation sensor are magnetic sensors.

25. Apparatus according to claim 19 and comprising a three-dimensional viewing device for three-dimensionally viewing said needle and said trajectory on said display screen.

26. Apparatus according to claim 19, wherein said imaging apparatus is computerized tomography apparatus and said imaging detector is a computerized tomography scanning head comprising a CT radiation source and a CT detector.

27. Apparatus according to claim 19, wherein said imaging apparatus is magnetic resonance imaging apparatus and said imaging detector is a magnetic resonance imaging scanning head comprising a MRI radiation source and a MRI detector.

28. Apparatus according to claim 19, wherein said imaging apparatus is X-Ray apparatus and said imaging detector is a X-Ray scanning head comprising a X-Ray radiation source and a X-Ray detector.

29. The apparatus of claim 19, wherein said at least a portion of said needle includes a point along said needle.

30. The apparatus of claim 19, wherein said at least a portion of said needle includes the tip of said needle.

31. The apparatus of claim 19, wherein said at least a portion of said needle includes at least substantially all of said needle.

32. The apparatus of claim 19, additionally comprising:

a connector adapted for attachment to said needle, said connector for connection to a sampling device.

33. An apparatus for directing of a needle with respect to a target located in a body volume, comprising:

a needle;

a needle orientation sensor attached to said needle which senses orientation of said needle with respect to a reference;

an imaging detector for transmitting an image to a display device;

a probe orientation sensor attached to said imaging detector for sensing orientation of said imaging detector with respect to said reference; and a position sensing controller in operative communication with said needle orientation sensor and said probe orientation sensor configured for determining the position of said displayed image from said spatial orientation data of said imaging detector and configured for placing a representation of at least one of the trajectory or the position of at least a portion of said needle on said image on said display device, based on said orientations of said imaging detector and said needle with respect to said reference.

34. The apparatus of claim 33, wherein said at least a portion of said needle includes a predetermined point along said needle.

35. The apparatus of claim 33, wherein said at least a portion of said needle includes the tip of said needle.

36. The apparatus of claim 33, wherein said at least a portion of said needle includes at least substantially all of said needle.

37. The apparatus of claim 33, additionally comprising:

a connector adapted for attachment to said needle, said connector for connection to a sampling device.

\* \* \* \* \*